(12) United States Patent
Modarres (10) Patent No.: US 7,860,561 B1
(45) Date of Patent: Dec. 28, 2010

(54) METHOD OF QUANTIFYING A SUBJECT'S WAKE OR SLEEP STATE AND SYSTEM FOR MEASURING

(75) Inventor: Mohammad Modarres, Cleveland Heights, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 1896 days.

(21) Appl. No.: 10/860,863

(22) Filed: Jun. 4, 2004

(51) Int. Cl.
*A61B 5/04* (2006.01)

(52) U.S. Cl. ..................................... 600/544

(58) Field of Classification Search .......... 600/544–545
See application file for complete search history.

(56) References Cited

U.S. PATENT DOCUMENTS

| | | | | |
|---|---|---|---|---|
| 5,311,877 | A * | 5/1994 | Kishi .......................... | 600/545 |
| 5,813,993 | A * | 9/1998 | Kaplan et al. ................ | 600/544 |
| 5,999,846 | A * | 12/1999 | Pardey et al. ................ | 600/544 |
| 6,161,030 | A | 12/2000 | Levendowski et al. | |
| 6,167,298 | A | 12/2000 | Levin | |
| 6,272,378 | B1 | 8/2001 | Baumgart-Schmitt | |
| 6,496,724 | B1 | 12/2002 | Levendowski et al. | |
| 6,549,804 | B1 * | 4/2003 | Osorio et al. ................ | 600/544 |
| 6,826,426 | B2 * | 11/2004 | Lange et al. ................. | 600/544 |
| 7,228,169 | B2 * | 6/2007 | Viertio-Oja et al. .......... | 600/544 |
| 7,299,088 | B1 * | 11/2007 | Thakor et al. ............... | 600/544 |
| 2004/0010203 | A1 * | 1/2004 | Bibian et al. ................. | 600/544 |
| 2004/0193068 | A1 * | 9/2004 | Burton et al. ................ | 600/544 |
| 2005/0076908 | A1 * | 4/2005 | Lee et al. ................ | 128/204.23 |

OTHER PUBLICATIONS

Ogilvie RD, & RT Wilkinson. Behavioral versus EEG-based Monitoring of All-Night Sleep/Wake Patterns. Sleep, 11, pp. 139-155, 1998.
Milter MM, Carskadon MA, Czeisler CA, Dement WC, Dinges DF, Graeber RC. Catastrophes, Sleep, and Public Policy: Consensus Report. Sleep, 12, pp. 458-474, 1989.
Guilleminault, C., R. Stoohs, and S. Duncan. Snoring(I): Daytime Sleepiness in Regular Heavy Snorers. Chest, 99, pp. 40-48, 1991.
Bennett, Langford, Stradling, et al. Sleep Fragmentation Indices in OSA. American Journal of Respiratory and Critical Care Medicine, 158, pp. 778-786, 1998.

(Continued)

*Primary Examiner*—Patricia C Mallari
*Assistant Examiner*—Karen E Toth
(74) *Attorney, Agent, or Firm*—Brian M. Kolkowski; Robert Knecht Schmidt (57) ABSTRACT

The present invention relates to a method of quantifying a subject's wake or sleep state, and more particularly to a higher resolution method of determining when a subject is awake or asleep. The present invention additionally relates more specific applications of this method, and a system for making these quantitative measurements. There are numerous embodiments of the present invention, which are envisioned, with a few of those listed below. The present invention relates to a method of analyzing a subject, and preferably a human subject to determine quantitatively when the subject is awake and when the subject is sleeping. The present invention has application for use with alertness devices, for use to better analyze sleeping disorders, anesthesia monitors, psychiatric and hypnosis medication monitoring, and for looking at the effect of various other therapies.

14 Claims, 8 Drawing Sheets

OTHER PUBLICATIONS

Thorpy, M.J. Report From the American Sleep Disorders Association: The Clinical Use of the Multiple Sleep Latency Test. Sleep, 15, pp. 268-276, 1992.
Milter, MM, et al. Maintenance of Wakefulness Test . . . Electroencephalography and Clinical Neurophysiology, 53, pp. 658-661, 1982.
Borin, Elliot. This Palm Reads Your Mind, http://www.wired.com/news/technology/0,1282,58809,00.html.
Ahmed, Mansoor. Excessive Daytime Sleepiness. Presentation.
Ahmed, Mansoor. Current Concepts in Insomnia. Presentation.
Ahmed, Mansoor. Sleep Disorders—a Serious Pulbic Health Issue. Presentation.
Sherry, Patrick. Fatigue Countermeasures in the Railroad Industry: Past and Current Developments. Published by Association of American Railroads, 2000.
Thomasson, W.A. APSS: Sleep Disorder Diagnosis Can Be Done Effectively at Home. http://www.pslgroup.com/dg/1fdc9A.htm.
Obstructive Sleep Apnea. http://www.pulmonarychannel.com/osa/diagnosis.shtml.
Correspondence from Advanced Brain Monitoring, Jan. 24, 2001.

* cited by examiner

METHOD OF QUANTIFYING A SUBJECT'S WAKE OR SLEEP STATE AND SYSTEM FOR MEASURING

BACKGROUND OF THE INVENTION

1. Field of the Invention

The present invention relates to a method of quantifying a subject's wake or sleep state, and more particularly to a higher resolution method of determining when a subject is awake or asleep. The present invention additionally relates more specific applications of this method, and a system for making these quantitative measurements.

2. Technical Background

Nearly one in seven people in the United States suffer from some type of chronic sleep disorder, and only fifty percent (50%) of people are estimated to get the recommended seven (7) to eight (8) hours of sleep each night. It is further estimated that sleep deprivation and its associated medical and social costs (loss of productivity, industrial accidents, etc) exceed $150 billion dollars per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life.

Excessive daytime sleepiness (EDS) is a symptom describing an increased propensity to fall asleep, often during monotonous or sedentary activities. Though sometimes difficult, EDS vs. fatigue need to be differentiated. Fatigue or lethargy is where a subject senses a lack of energy or physical weakness and may not have an increased propensity to fall asleep at an inappropriate time. The underlying etiology of EDS generally falls into three categories: chronic sleep deprivation, circadian disorders (shift work), and sleep disorders. EDS is currently diagnosed via two general methods. The first is via subjective methods such as the Epworth and Standford Sleepiness Scale, which generally involves questionnaires where the patients answer a series of qualitative questions regarding their sleepiness during the day. With these methods, however, it is found that the patients usually underestimate their level of sleepiness or they deliberately falsify their responses because of their concern regarding punitive action, or as an effort to obtain restricted stimulant medication.

The second is via physiological based evaluations such as all night polysomnography to evaluate the patients sleep architecture (e.g., obtaining respiratory disturbance index to diagnose sleep apnea) followed by an all day test such as the Multiple Sleep Latency Test (MSLT) or its modified version, Maintenance of Wakefulness Test (MWT). The MSLT consists of four (4) to five (5) naps and is considered the most reliable objective measure of sleepiness to date. The MSLT involves monitoring the patient during twenty (20) to forty (40) minute nap periods in two-hour intervals one and one half hour (1.5 hrs) to three hours (3 hrs) after awakenings to examine the sleep latency and the sleep stage that the patient achieves during these naps, i.e., the time it takes for the patient to fall asleep. A sleep disorder such as narcolepsy for example is diagnosed when the patient has a restful night sleep the night before but undergoes rapid eye movement sleep (REM sleep) within five (5) minutes of the MSLT naps. The MWT is a variation of the MSLT. The MWT provides an objective measure of the ability of an individual to stay awake.

While the MSLT and MWT are more objective and therefore don't have the same limitations as mentioned for the subjective tests, the MSLT and MWT have their own limitations. Both the MSLT and MWT require an all-day stay at a specialized sleep clinic and involve monitoring a number of nap opportunities at two hour intervals throughout the day. Further, the MSLT mean sleep latency is only meaningful if it is extremely short in duration (e.g., to diagnose narcolepsy), and only if the overnight polysomnogram does not show any sleep disordered breathing. Another problem with the MSLT mean sleep latency is the so-called "floor effect" where the sleep latency in the pathologically sleepy patients can be almost zero (0) minutes, i.e., the patient falls asleep almost immediately following turning off the light in the MSLT test. This type of result has a tendency to limit the diagnostic resolution of the test. Finally, studies have shown that the MSLT is not particularly suited for gauging the effects of therapeutic intervention. This was demonstrated in studies by Thorpy in 1992 and Van den Hoed et al. in 1981 showing no reliable reduction in sleepiness in patients given stimulant medications for narcolepsy.

The MWT was developed in 1982, in part, to address some of the short-comings of the MSLT method. The MWT eliminated the "floor effect" in the MSLT test shown in narcoleptic patients due to the instruction in the MWT test to the patient to stay awake. The MWT, however, created another problem at the other end of the sleep latency period called the "ceiling effect". The "ceiling effect" is the tendency of less "sleepy" individuals to perform the MWT without falling asleep. In fact, the length of the MWT trial was lengthened from twenty (20) to fourty (40) minutes in 1984 because it was observed that patients with histories of excessive daytime sleepiness were too often able to maintain wakefulness for the twenty (20) minutes. In addition, while the MSLT and MWT are objective and "broadly" quantitative tests in that they both require the patient to fall asleep during the test and they measure the number of those incidents of sleep during the testing regiment, these tests are too costly and lack the degree of quantitative resolution necessary to easily permit measurement of effects of therapeutic intervention and degrees.

In recent years there have been a number of efforts to develop systems for detecting alertness and drowsiness by attempting to quantify the brain waves of a subject. Most of these systems have been aimed at the alertness monitoring field for alertness critical applications. Examples of these types of systems are as follows: Levin U.S. Pat. No. 6,167,298 discloses a device for monitoring and maintaining an alert state of consciousness for a subject wearing the device. With this device an alert mental state is maintained through monitoring of brain wave patterns to detect if a transition from an alert to a non-alert mental state is about to occur, or has occurred. If so, the device provides a stimulus until such time as an alert mental state, as assessed by the brain wave activity, is restored. Levendowski et al. U.S. Pat. No. 6,496,724 discloses a method of classifying individual EEG patterns along an alertness-drowsiness classification continuum. The results of the multi-level classification system are applied in real-time to provide feedback to the user via an audio or visual alarm, or are recorded for subsequent off-line analysis. Kaplan et al. U.S. Pat. No. 5,813,993 discloses an alertness and drowsiness detection and tracking system. The system claims improved performance by preserving and analyzing brain wave signal components at frequencies above 30 Hz.

Most of the methods, systems or devices currently on the market either provide a qualitative means for analyzing for excessive daytime sleepiness or more specifically for sleep disorders, or a semi-quantitative means for classifying a subjects state of alertness. None of the above mentioned methods, systems or devices provide a quantitative means of measuring and determining whether an individual suffers from excessive daytime sleepiness and more specifically from a sleeping disorder, particularly one in which the analysis and measurement are capable of being provided in a short time duration and at low cost to the patient or insurance company. Furthermore none of the above mentioned methods provide a method with the sensitivity for very accurately quantifying the degree of sleepiness or alertness, i.e., micro-arousals or micro-sleep. It is therefore an object of the present invention to provide a quantitative method of analysis wherein it can be determined whether a patient exhibits excessive daytime sleepiness. It is still another object of the present invention to provide a method of more accurately determining the wake-sleep transition. It is still another object of the present invention that this method be inexpensive and/or of short time duration. It is still another object of the present invention that a patient's therapeutic treatment can be more accurately determined based on these methods, and can subsequently be adjusted accordingly based on a subsequent test of the patient.

SUMMARY OF THE INVENTION

The present invention relates to a method of quantifying a subject's wake or sleep state, and more particularly to a higher resolution method of determining when a subject is awake or asleep. The present invention additionally relates more specific applications of this method, and a system for making these quantitative measurements.

There are numerous embodiments of the present invention, which are envisioned, with a few of those listed below. The present invention relates to a method of analyzing a subject, and preferably a human subject to determine quantitatively when the subject is awake and when the subject is sleeping. The present invention has application for use with alertness devices, for use to better analyze sleeping disorders, anesthesia monitors, psychiatric and hypnosis medication monitoring, and for looking at the effect of various other therapies.

More accurate and higher resolution characterization of wake-sleep states using EEG analysis allows for more accurate quantification between the transition from wakefulness and sleep. The higher resolution of the method of the present invention is important among other things for the proper diagnosis of sleepiness. The method allows for more accurate characterization of the depth of sleep in a given sleep stage including characterizing and defining micro-arousals and micro-sleep. Microarousals can have a significant inpact on the quality of the subject's sleep. For example, this quantification or improved resolution allows brief awakenings or the shallowness of lighter sleep stages that might not even reach a micro-arousal stage but are close enough to the awake state to severely deteriorate the quality of sleep resulting in fatigue and sleepiness during the day for a subject, to be viewed. Automatic and/or real-time implementation of these methods allows for numerous applications some of which are mentioned above. Further, these methods allow for systems with fewer EEG electrodes, which are currently not routinely available to subject's today.

In one embodiment the present invention includes a method of quantifying wake-sleep states comprising the steps of using at least one sensor to measure the subject's brain wave signals over a measurement time period, the measurement time period comprising a number of time segments; analyzing the subject's brain wave signals to estimate or determine a power spectrum profile, indices or index for each time segment; performing a wavelet decomposition on the power spectrum profile, indices or index over the measurement time period; analyzing the subject's brain wave signals to estimate or determine a dominant frequency profile, indices or index for each time segment; performing a wavelet decomposition on the dominant frequency profile, indices or index over the measurement time period; and determine a wake-sleep transition based in part on the results of performing the wavelet decomposition on the power spectrum in the previous step and in part on the results on the results of performing a wavelet decomposition on the dominant frequency from another previous step.

In one embodiment, the present invention includes a method of quantifying wake-sleep states comprising the steps of using at least one sensor to measure the subject's brain wave signals over a measurement time period, the measurement time period comprising a number of time segments; analyzing the subject's brain wave signals to estimate or determine a power spectrum profile, indices or index for each time segment; and performing a wavelet decomposition on the power spectrum profile, indices or index over the measurement time period.

In another embodiment, the present invention includes a method of quantifying wake-sleep states comprising the steps of using at least one sensor to measure the subject's brain wave signals over a measurement time period, the measurement time period comprising a number of time segments; analyzing the subject's brain wave signals to estimate or determine a dominant frequency profile, indices or index for each time segment; and performing a wavelet decomposition on the dominant frequency profile, indices or index over the measurement time period.

In still another embodiment, the present invention includes a method of quantifying wake-sleep states comprising the steps of using at least one sensor to measure the subject's brain wave signals over a measurement time period; analyzing the subject's brain wave signals to estimate or determine a time varying frequency spectral characteristics; and performing a wavelet decomposition on the time varying frequency spectral characteristics over the measurement time period.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENTS

The present invention relates to a method of quantifying a subject's wake or sleep state, and more particularly to a higher resolution method of determining when a subject is awake or asleep. The present invention additionally relates more specific applications of this method, and a system for making these quantitative measurements.

The present invention involves the step of using at least one sensor to measure a subject's brain wave signals over a period of time. The brain wave or EEG signals can be obtained by any method know in the art, or subsequently developed by those skilled in the art to detect these types of signals. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subjects scalp. The subject(s) referred to in the present invention can be any form of animal. Preferably the subject(s) are mammal, and most preferably human.

If electrodes are used to pick up the brain wave signals, these electrodes may be placed at one or several locations on the subject(s)' scalp or body. The electrode(s) can be placed at various locations on the subject(s) scalp in order to detect EEG or brain wave signals. Common locations for the electrodes include frontal (F), parietal (P), anterior (A), central (C) and occipital (O). Preferably for the present invention at least one electrode is placed in the occipital position. In order to obtain a good EEG or brain wave signal it is desirable to have low impedances for the electrodes. Typical EEG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used—one signal electrode and one reference electrode; and if further EEG or brain wave signal channels are desired the number of electrodes required will depend on whether separate reference electrodes or a single reference electrode is used. For the various embodiments of the present invention, preferably an electrode is used and the placement of at least one of the electrodes is at or near the occipital lobe of the subject's scalp.

The present invention has application for use with any device where it would be helpful to more accurately detect a subject's wake-sleep cross-over. The applications include but are not limited to use with alertness devices, sleep analysis devices, anesthesia monitors, psychiatric and hypnosis medication monitoring, and for looking at the effect of various other therapies. In any of these types of applications, preferably, the subject's brain wave or EEG signals are collected. The signals can be collected through conventional recorders, analog signal processors or similar other devices and analyzed after collection, however, given the easy access to digital technology such as processors and computers preferably the collection and analysis of the brain wave or EEG signals is carried out nearly concurrently (or simultaneously) using these digital means. The subject's brain wave signals are recorded or measured over a measurement time period, or the period of time necessary to perform the test or method. In one embodiment of the present invention, a processor or computer receives digitized signals based on analog signals from the sensor used to measure the subject's brain wave or EEG signals.

Figure 1:
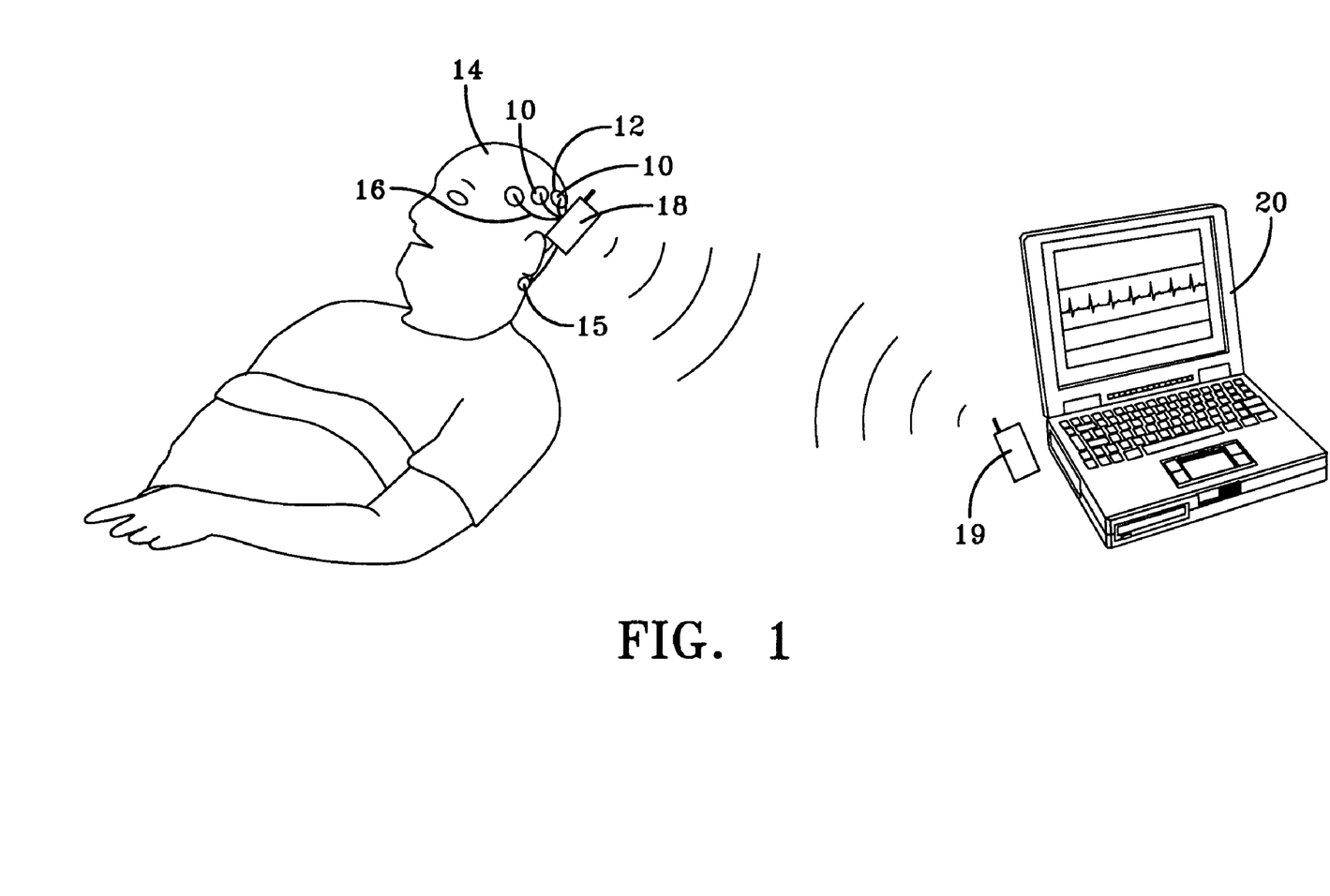
FIG. 1. is an illustration of a subject wearing a sensor to pickup and transmit brain wave signals to a computer for quantitatively analyzing the subject sleep and wake states.

The various embodiments of the method of the present invention can be used in numerous systems as well as in numerous applications. An embodiment of a system which incorporates the methods of the present invention is shown in FIG. 1. FIG. 1 is an illustration of a subject wearing a sensor to pickup and transmit brain wave signals to a computer for quantifying a subject's wake sleep state. In FIG. 1, an electrode (sensor) 10 is placed on the central lobe 12 of the subject's scalp 14, and another reference electrode (sensor) 10 is placed behind the subject's ear 15. The electrodes 10 are dry electrodes. The electrodes 10 are releasable connected to leads 16 which can be connected to a processing unit (not shown) or to a wireless telemetry unit 18, which transmits the raw brain wave or EEG signal to a receiver 19 and then processing unit 20 for analysis. It is clear to someone skilled in the art where the placement of the electrode 10 will be required in order to maintain a close proximity between the electrode 10 and that portion of the brain. The number of electrodes 10 and likewise signals to be analyzed depends on the environment in which the sleep analysis system is to be used. In a more formal setting, it may be desirable to collect and analyze multiple brain wave or EEG signals from several locations on a subject's scalp. In a less formal setting such as a family practitioner's, internist's or general practitioner's office, it may be desirable to apply one sensor that requires little or no expertise in placement of the electrode, i.e., a dry electrode. The electrodes can preferably be placed in the locations of the frontal (F), parietal (P), anterior (A), central (C) and occipital (O) lobes of the brain.

Most preferably, the system that incorporates all or part of the methods of the present invention includes a wireless amplifier/transmitter unit. More preferably, the amplifier/transmitter unit, is a lightweight (3.4 oz with 2 batteries) and small (4.0"×2.2"×0.7") wireless data acquisition unit (manufactured by Cleveland Medical Devices Inc. and known as Crystal™ EEG). This wireless data acquisition unit is capable of measuring up to 8 channels of EEG in a highly dynamic environment and transmitting them at via a 902 to 928 MHz frequency shift key telemetry link to a commercial PC computer. The transmission range is approximately 100 feet. In addition, preferably the hardware includes at least one sensor. More preferably, an electrode wiring harness is used capable of handling multiple electrodes. The sensor(s) (or electrode(s)) of the present invention, preferably are connected with the amplifier/transmitter unit. The amplifier/transmitter unit is capable of communicating with a amplifier/transmitter unit which is hooked to the serial port of a laptop PC.

During or after brain wave data or signal collection analysis is performed on the data or signals. Preferably, the sampled brain wave or EEG signals are band-pass filtered in preferably the 0.1 Hz to 50 Hz range using a digital filter, e.g. a butterworth filter. This is followed by an optional step of artifact detection and removal (both a type of pre-filtering). Preferably, in the first step of analysis after data collection, the artifacts in the data are preferably identified and removed. In artifact detection and removal, the band-pass filtered data of the brain wave or EEG sample is compared with the standard deviation of the brain wave or EEG sample over the entire test or a portion of the test in which that sample is taken. If the brain wave or EEG sample is greater than some multiple of the standard deviation, preferably greater than about 3 times and more preferably greater than about 5 times, then that EEG sample is marked as an artifact and is replaced by a value that is derived from the artifact-free segment of the data immediately before. The artifact-free segment of data is that portion of the sampling data preferably greater than about 0.1 seconds before and also preferably less than about 0.6 before the artifact in sampling time. This pre-filtered brain wave or EEG sample data is then filtered or analyzed using either non-parametric or parametric filtering techniques.

Figure 2:
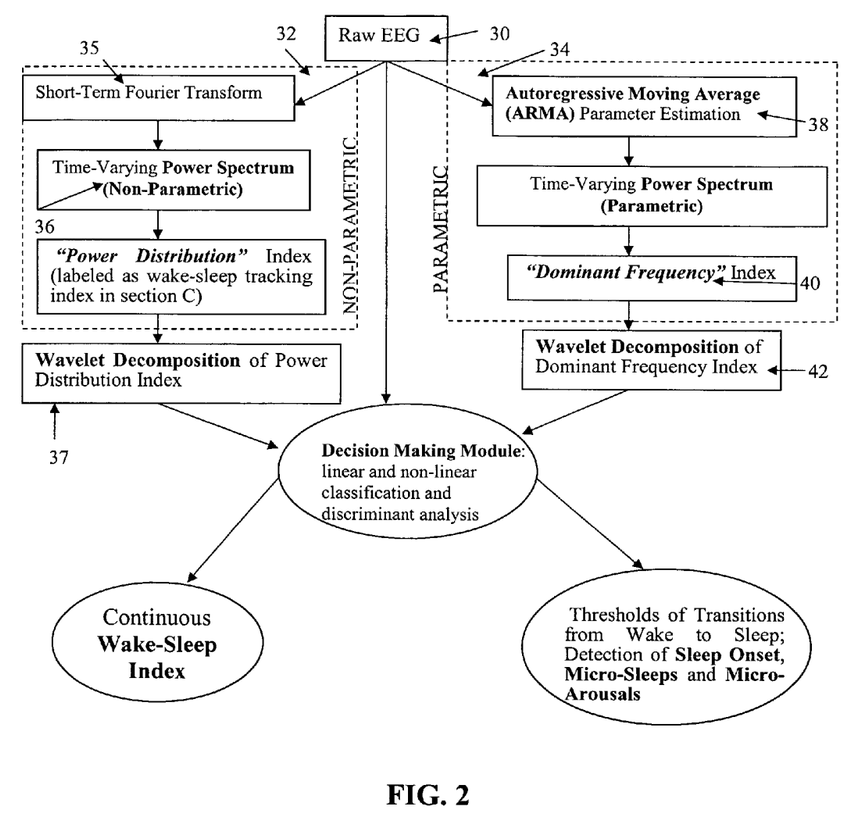
FIG. 2. is a flow diagram demonstrating the signal analysis or filtering used in several embodiments of the present invention.

FIG. 2 is a flow diagram demonstrating a hybrid type of signal analysis or filtering methods used in several embodiments of the present invention. FIG. 2 shows the conceptual structure of these novel class of EEG or brain wave data or signal analysis algorithms for quantifying wake-sleep states. In FIG. 2, the raw brain wave signals or data are collected from a single electrode (or sensor) 30 over a measurement time period. These brain wave data or signals can be analyzed over this measurement time period or over a number of various time periods comprising the measurement time period. These raw brain wave signals or data can optionally be pre-filtered to remove artifacts (not shown). The raw brain wave signals or data or pre-filtered signals or data is then directly filtered using either or both the non-parametric 32 or parametric 34 filtering techniques, which are used to enhance various characteristics of the signal, e.g., power distribution or index; dominant frequency index, etc. One example of a non-parametric filtering technique is using a Short Fourier Transform 35. By filtering the brain wave data or signal, a time-varying power spectrum profile, indices or index 36 is obtained describing the instantaneous power distribution (e.g., relative power in different bands such as alpha, theta, delta, and beta). The power spectrum profile, indices or index 36 is then analyzed or filtered using a wavelet decomposition 37 to obtain the higher sensitivity or resolution trends and details of the profile, indices or index 36. At the same or different times the same raw brain wave signal or data is subjected to another parametric filtering technique 34. One example of a parametric filtering technique is to use Autoregressive modeling 38. By filtering the brain wave data or signal, a time-varying dominant frequency profile, indices or index 40 is obtained. The dominant frequency profile, indices or index 40 produces sharper, higher resolution peaks at the dominant frequency at the expense of not preserving as accurate power values. The dominant frequency profile, indices and index 40 is then analyzed or filtered using a wavelet decomposition 42 to obtain the higher sensitivity or resolution trends and details of the profile, indices or index 40. The resulting profile, indices or index from each of the two filtering techniques are then used in part to more accurately track the wake and sleep transitions and to determine a threshold for alertness, drowsiness, sleep onset and micro-arousals.

Figure 3:
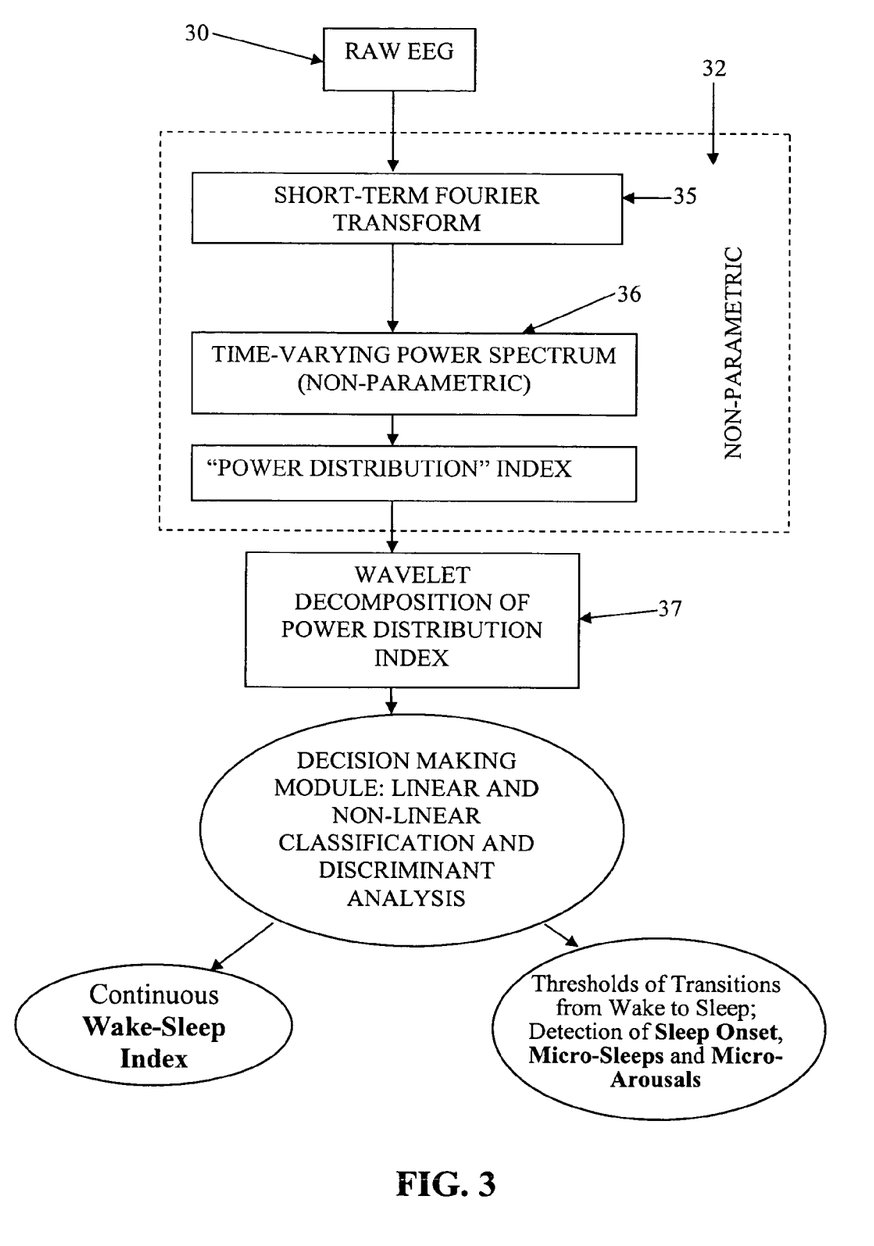
FIG. 3 is a flow diagram demonstrating a hybrid signal analysis or filtering methods using non-parametric based filtering or signal analysis.

FIG. 3 is a flow diagram demonstrating a hybrid signal analysis or filtering methods using non-parametric based filtering or signal analysis. FIG. 3 shows the conceptual structure of this novel class of hybrid EEG or brain wave data or signal analysis algorithms for quantifying wake-sleep states. In FIG. 3, the raw brain wave signals or data are collected from a single electrode (or sensor) 30 over a measurement time period. These brain wave data or signals can be analyzed over this measurement time period or over a number of various time periods comprising the measurement time period. These raw brain wave signals or data can optionally be pre-filtered to remove artifacts (not shown). The raw brain wave signals or data or pre-filtered signals or data is then directly filtered using a non-parametric 32 filtering technique, in this embodiment by using a Short Fourier Transform 35. By filtering the brain wave data or signal, a time-varying power spectrum profile, indices or index 36 is obtained describing the instantaneous power distribution (e.g, relative power in different bands such as alpha, theta, delta, and beta). The power spectrum profile, indices or index 36 is then analyzed or filtered using a wavelet decomposition 37 to obtain the higher sensitivity or resolution trends and details of the profile, indices or index 36. The resulting profile, indices or index from this hybrid filtering technique is then used in part to more accurately track the wake and sleep transitions and to determine a threshold for alertness, drowsiness, sleep onset and micro-arousals.

Figure 4:
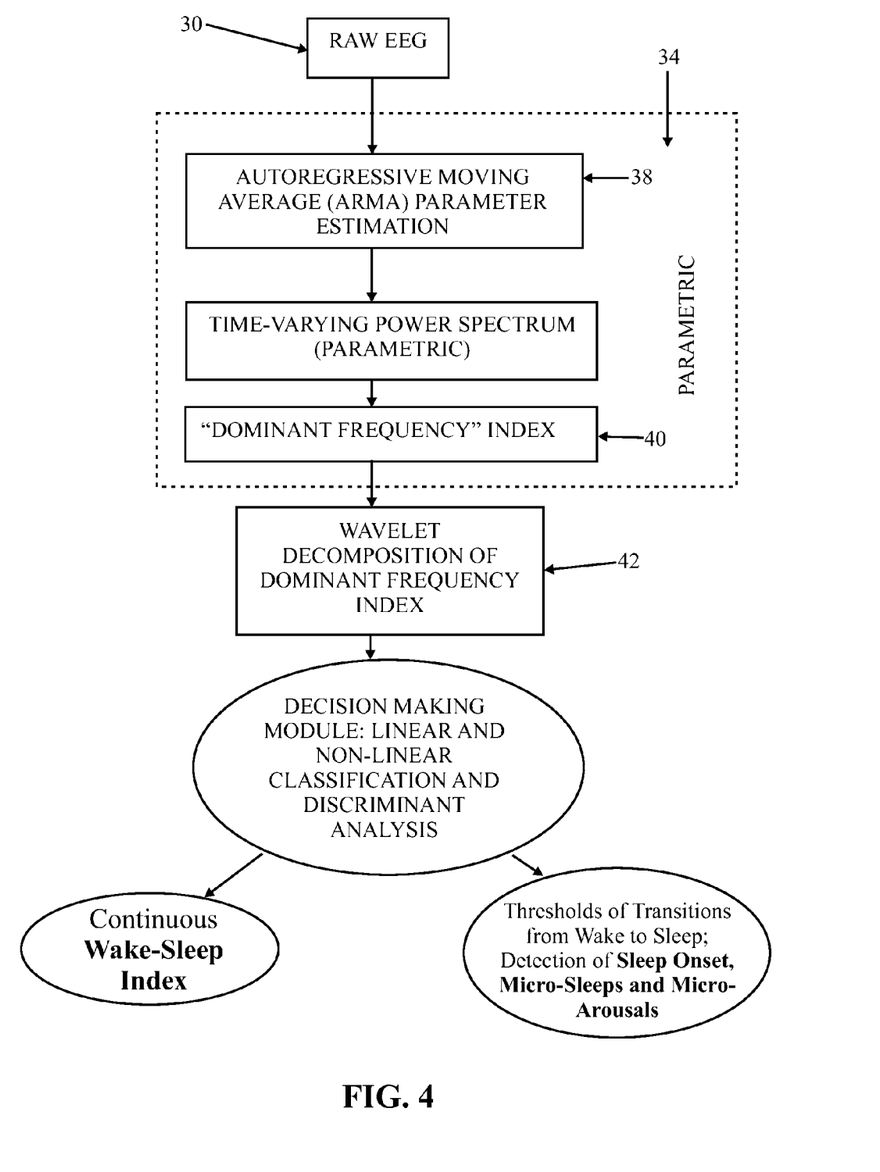
FIG. 4 is a flow diagram demonstrating a hybrid signal analysis or filtering methods using parametric based filtering or signal analysis.

FIG. 4 is a flow diagram demonstrating a hybrid signal analysis or filtering methods using a parametric based filtering or signal analysis. FIG. 4 shows the conceptual structure of this novel class of hybrid EEG or brain wave data or signal analysis algorithms for quantifying wake-sleep states. In FIG. 4, the raw brain wave signals or data are collected from a single electrode (or sensor) 30 over a measurement time period. These brain wave data or signals can be analyzed over this measurement time period or over a number of various time periods comprising the measurement time period. These raw brain wave signals or data can optionally be pre-filtered to remove artifacts (not shown). The raw brain wave signals or data or pre-filtered signals or data is then directly filtered using a parametric 34 filtering technique, in this embodiment by using a Autoregressive Moving Average 38. By filtering the brain wave data or signal, a time-varying power spectrum profile, indices or index 40 is obtained describing the dominant frequency of the EEG from the parameters of the model. The dominant frequency profile, indices or index 40 is then analyzed or filtered using a wavelet decomposition 42 to obtain the higher sensitivity or resolution trends and details of the profile, indices or index 40. The resulting profile, indices or index from this hybrid filtering technique is then used in part to more accurately track the wake and sleep transitions and to determine a threshold for alertness, drowsiness, sleep onset and micro-arousals.

Preferably, the subject's brain wave signals are analyzed using a non-parametric filtering technique. The use of a non-parametric analysis or filtering of a subject's brain wave signal or data is described in more detail below. For this analysis or filtering, more preferably, the subject's brain wave or EEG sample over the measurement time period is preferably broken into consecutive sampling moments or time segments. These sampling moments or time segments are preferably 2 seconds in duration allowing for example 400 sampling points if the brain wave or EEG signal sampling rate was 200 samples per second. Each consecutive time segment is then transformed into a frequency domain representation (also known as power spectrum or frequency power spectrum) using techniques known to those skilled in the art. One technique, which is preferred, is to use a standard Fast Fourier Transform method (FFT). The FFT coefficients obtained are then squared and scaled to obtain the power spectrum plot (i.e., the power of brain wave or EEG signal at each frequency level). In this embodiment since the segment duration is for 2 seconds, the frequency resolution will be 0.5 Hz, and power values can be obtained for frequency bins of 0.5, 1, 1.5, 2, 2.5, . . . , 50 Hz.

The power spectrum of each time segment is used to determine if the time segment contains movements and other types of artifacts. Some of the artifacts manifest themselves in abnormally large power values in all frequencies, particularly at very low frequencies <10 Hz, compared to the power spectrum of the entire study. Upon detection of such abnormally high power spectra, preferably the entire sampling segment (in this embodiment 2 seconds) is marked as contaminated by the artifacts and is replaced by an average power spectrum of the artifact-free segments.

Brain wave data that is monitored and analyzed according this embodiment of the present invention is between about 0.1 to about 50 Hz. Preferably, between 0.1 to about 30 Hz, more preferably between about 0.1 to about 15 Hz, and most preferably between about 0.1 to about 13 Hz. Also in certain embodiments of the present invention brain waves are categorized as delta, theta, alpha and beta waves or components. Delta waves or components generally exhibit brain wave or EEG activity in the frequency range from about 1 Hz to about 4 Hz, theta waves or components generally in the frequency range from about 6 Hz to about 7.5 Hz, alpha waves or components generally in the frequency range from about 7.5 Hz to about 13 Hz, and beta waves or components generally in the frequency range from about 13 Hz to about 30 Hz. As those skilled in the art will appreciate, the boundaries between these components are somewhat arbitrary. Thus, the foregoing delineations are intended to be exemplary and not limiting. Furthermore, use of other components, whether now known or later discovered, are within the scope of the invention.

The subject's brain wave signals as described above may also be analyzed using a parametric filtering technique. This analysis or filtering technique belongs to the general family of time-series modeling. It models the signal as a linear combination of its past values (auto-regressive) along with present and past white noise (moving average). Unlike, non-parametric analysis or filtering such as FFT, parametric analysis or filtering does not assume that the data outside the analyzing window is zero. This results in a much sharper spectral decomposition. If a parametric analysis or filter is used, preferably, an Autoregressive Moving Average (ARMA) is used such as $$X(n)=a_1X(n-1)+ \ldots +a_pX(n-p)+ \ldots + \ldots + b_0W(n)+ \ldots b_mW(n-m)$$

where X is the data vector (EEG), n is the time index, and W(n) is a white noise sequence. The ARMA parameters $\{a_1, \ldots, a_p, b_0, \ldots, b_m\}$ are estimated from minimizing the prediction-error. This is the difference between the measured signal and its predicted value using the ARMA parameters. An important consideration with this method is with regards to choosing the model order which refers to the number of past values (i.e., number of a's and b's) to include in the estimation method. The larger this model order, the more likelihood of accurately modeling discrete oscillations that might be present in the data. This comes, however, at the expense of more computational demand and reduced confidence of the parameters thus requiring large data or time segments which reduces the frequency resolution. For spectral analysis using this analysis or filtering method, z-transform is performed on the ARMA such as $$H(z)=[b_0+b_1z^{-1}+ \ldots ]/[1+a_1z^{-2}+ \ldots ]$$

by substituting $Z=ej\omega$ in this equation, where $\omega$ corresponds to angular frequency, a frequency response equation can be obtained from which one can compute the spectrum from the magnitude of $|H(\omega)|$. The dominant frequency index is then computed from the parametric power spectrum of the above by identifying the frequency with the highest concentrated power.

Once EEG sample data is filtered or analyzed using either non-parametric or parametric filtering techniques the resultant power spectrum profile, indices or index (for non-parametric techniques) or dominant frequency profile, indices or index (for parametric techniques) is further filtered or analyzed by performing a wavelet analysis or decomposition. Preferably, a wavelet transform is used to decompose predefined epochs of the profile, indices or index into a set of coefficients a and $d_j$ such as $$x \rightarrow \{\{a;d_j\}, j=1, 2 \ldots L\}$$

where L is the level of decomposition, vector $d_j$ represents the signal details in specific frequency bands $d_j$, while a represents the signal approximation at the highest level of decomposition. The signal is then reconstructed at each detail level using an inverse wavelet transform.

Figure 5:
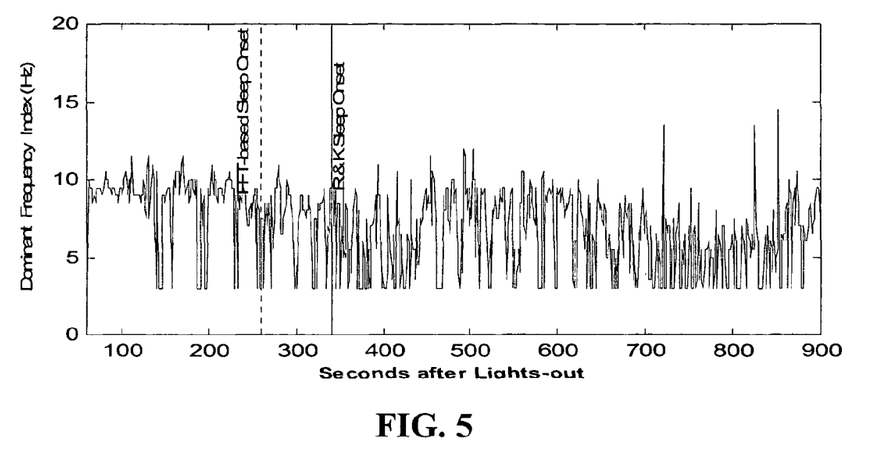
FIG. 5 is a graph showing a subject's brain wave signal using only a parametric based filter.

FIG. 5 is a graph showing a subject's brain wave signal using only a parametric based filter (ARMA). In FIG. 5, a subject's brain wave signal was analyzed using only a parametric filter. The graph shows, as the subject got closer to a sleep onset time, the dominant frequency became highly variable dropping to mostly theta range after sleep onset. This graph further shows the difficulty in determining the wake-sleep transition only using one level of filtering of the brain wave signal, i.e., parametric or non-parametric without further wavelet decomposition.

Figure 6:
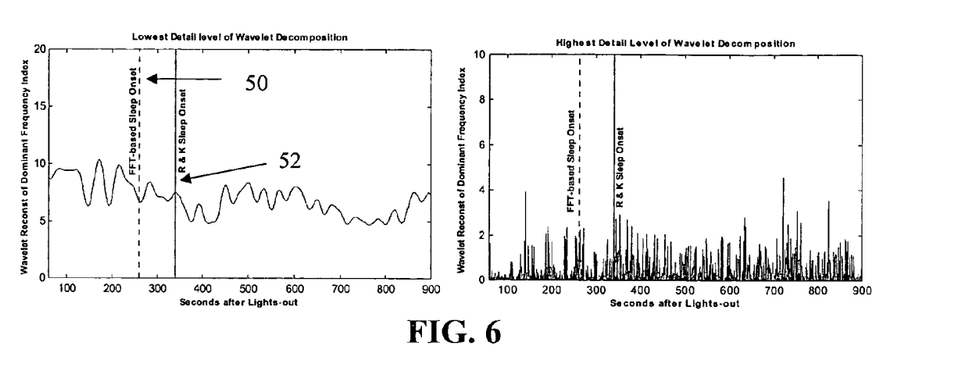
FIG. 6 is a graph showing a subject's brain wave signal using a double or hybrid filter (parametric filter and wavelet decomposition).

FIG. 6 is a graph showing a subject's brain wave signal using a double or hybrid filter (parametric filter and wavelet decomposition). In FIG. 6, the same subject's brain wave signal is analyzed using one embodiment of the hybrid filter. This graph further is constructed using the low frequency component trend of the index with time periods in the 2-4 second range. From this graph, it is clear that the dominant frequency started shows fluctuations 50 evident of sleep onset more than two minutes before the sleep onset time 52 scored by a polysonnogram technologist.

Figure 7:
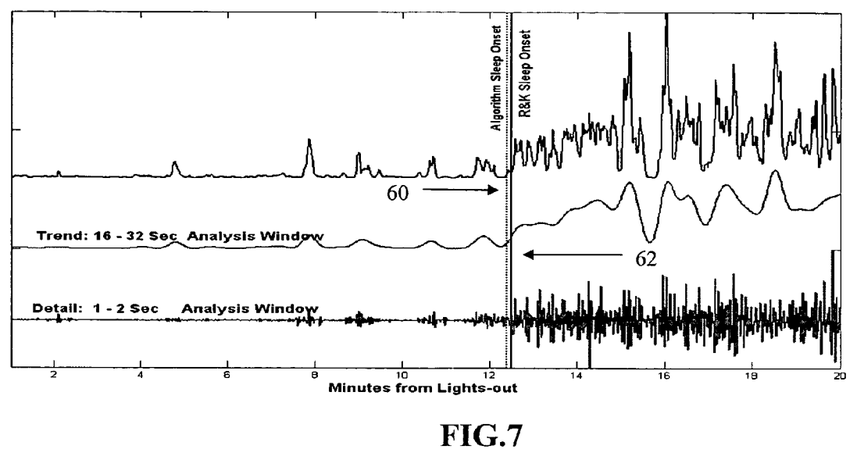
FIG. 7 is a graph showing a subject's brain wave signal using a double or hybrid filter (non-parametric filter and wavelet decomposition).

FIG. 7 is a graph showing a subject's brain wave signal using a double or hybrid filter (non-parametric filter and wavelet decomposition). In FIG. 7, the same subject's brain wave signal is analyzed using one embodiment of the hybrid filter. From this graph, it is clear that the power spectrum shows fluctuations 60 evident of sleep onset significantly before the sleep onset time 62 scored by a polysonnogram technologist.

Figure 8:
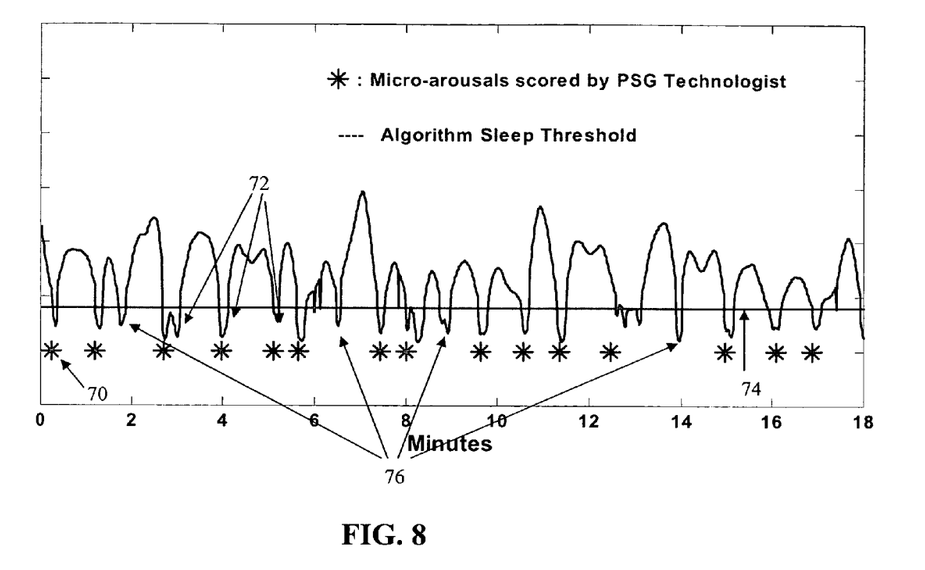
FIG. 8 is a graph showing a subject's brain wave signal using the hybrid filter technology of the present invention to determine microarousals.

FIG. 8 is a graph showing a subject's brain wave signal using the hybrid filter technology (non-parametric filter and wavelet decomposition) of the present invention to determine microarousals. In FIG. 8, the microarousals 70 scored by the polysonnogram technologist are determined by using data from not only a EEG, but EOG and EMG data as well. The microarousals 72 were scored by the hybrid algorithms of the present invention by establishing a threshold 74. As is show in FIG. 8 there are a number of microarousals 76 not noted by the polysonnogram technologist using more complex testing methods, which can be predicted by the hybrid algorithms of the present invention.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of quantifying wake-sleep states comprising the steps of:
   a) using at least one sensor to measure a subject's brain wave signals over a measurement time period, the measurement time period comprising a number of time segments;
   b) analyzing with a computer processor the subject's brain wave signals to estimate or determine a dominant frequency profile; dominant frequency indices or dominant frequency index for each time segment; and
   c) performing with the computer processor a wavelet decomposition on the dominant frequency profile, indices or index over the measurement time period.

2. The method of claim 1, further comprising the steps (d) analyzing the subject's brain wave signals to estimate or determine a power spectrum profile, power spectrum indices or power spectrum index for each time segment; and (e) performing a wavelet decomposition on the power spectrum profile, indices or index over the measurement time period.

3. The method of claim 2, further comprising the step of determining a wake-sleep transition based in part on the results of performing the wavelet decomposition on the power spectrum in the previous step (c) and in part on the results on the results of performing a wavelet decomposition on the dominant frequency from step (e).

4. The method of claim 1, wherein a wake-sleep transition can be determined in real time.

5. The method of claim 1, further comprising the step of quantifying the subject's overall sleep over the measurement time period.

6. The method in claim 1, wherein the method is used to trigger an alert to the subject.

7. A method of quantifying wake-sleep states comprising the steps of:
   a) using at least one sensor to measure a subject's brain wave signals over a measurement time period;
   b) analyzing with a computer processor the subject's brain wave signals to estimate or determine time-varying frequency spectral characteristics; and
   c) performing with the computer processor a wavelet decomposition on the time-varying frequency spectral characteristics over the measurement time period.

8. The method of claim 7, wherein a wake-sleep transition can be determined in real time real time.

9. The method of claim 7, further comprising the step of quantifying the subject's overall sleep over the measurement time period.

10. The method in claim 7, wherein the method is used to trigger an alert to the subject.

11. The method in claim 10, wherein the alert is either an alarm or a physical stimulus.

12. The method in claim 1, wherein the method is used to adjust the subject's sleep medication.

13. The method in claim 1, wherein the method is used to adjust the subject's sleep therapy.

14. The method in claim 1, wherein the method is used to research medications which can be used for sleeping disorders.

* * * * *